Oct. 14, 1958 G. DE RUITER Plant Pat. 1,763
ROSE PLANT
Filed March 3, 1958
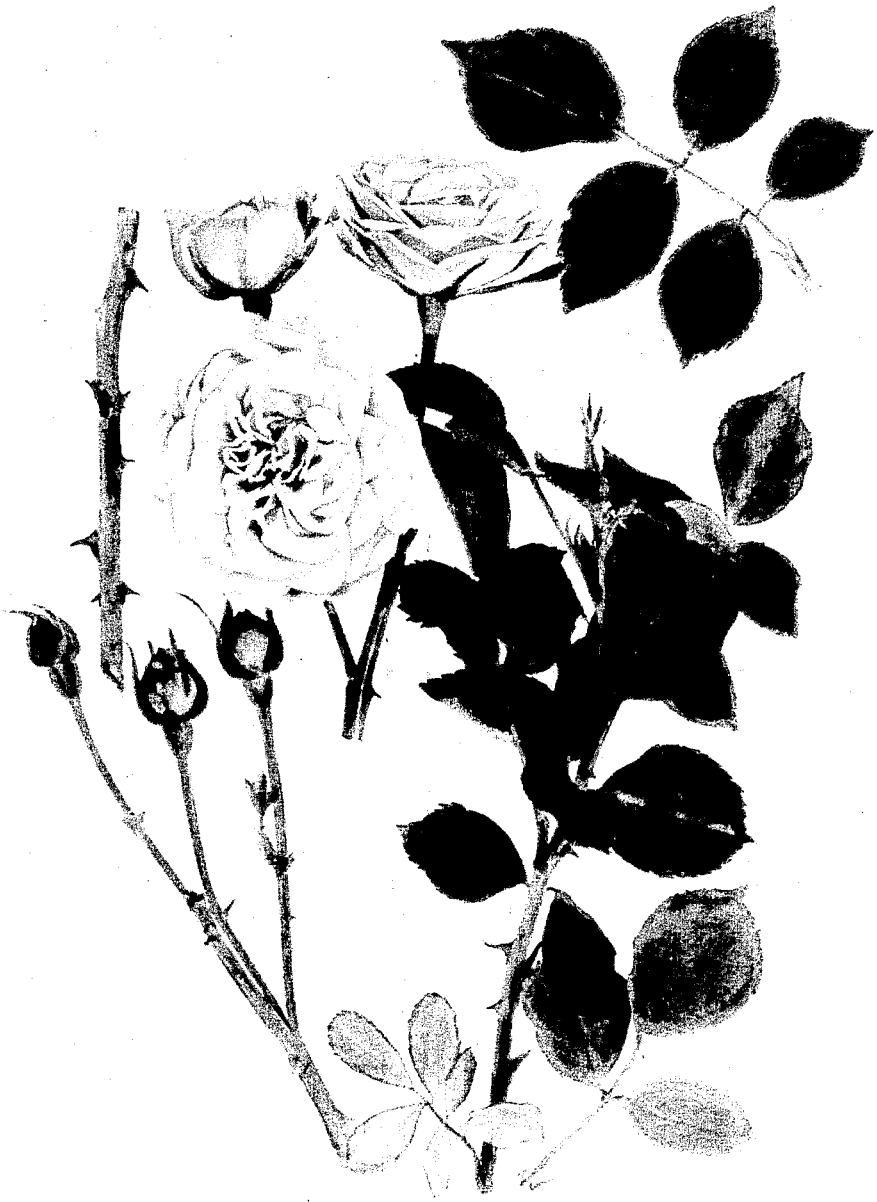
Inventor.
Gerrit de Ruiter
By: Robb & Robb
Attorneys.

United States Patent Office

Plant Pat. 1,763
Patented Oct. 14, 1958

1,763

ROSE PLANT

Gerrit de Ruiter, Hazerswoude, Netherlands, assignor to The Conard-Pyle Company, West Grove, Pa., a corporation of Pennsylvania Application March 3, 1958, Serial No. 718,935

1 Claim. (Cl. 47—61)

The present invention relates to a new and distinct variety of rose plant of the hybrid polyantha class, which was originated by me by crossing the variety "Rosemary" (unpatented) with an unnamed and unpatented seedling derived from a cross of "Sweetheart" (unpatented) with an unnamed and unpatented polyantha seedling.

As the result of this breeding, I have produced a new rose variety which combines therein the most desirable characteristics of its two parents, and which is particularly characterized as to novelty by a unique and desirable combination of features, the most outstanding of which are as follows:

(1) A dense and compact habit of growth;

(2) Excellent foliage;

(3) A very free flowering habit in the greenhouse and out of doors;

(4) Consistently uniform distribution of the blooms on the plant;

(5) Very double, long-lasting blooms;

(6) A distinctive Spirea Red general color tonality of the blooms; and (7) Exceptionally good suitability for greenhouse pot forcing.

The foregoing characteristics and distinctions definitely differentiate my new variety from its parents, as well as from all other varieties of its class of which I am aware, and the unique combination of its features makes the new variety valuable and desirable for both garden decoration and cut flowers as well as for pot forcing.

Asexual reproduction of the new variety by budding, as performed by me in Holland, and as performed on my behalf at West Grove, Pennsylvania, U. S. A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Color Chart of the Royal Horticultural Society, except where general color terms of ordinary dictionary significance are obvious:

Type: Hardy; bush; outdoor and greenhouse pot plants; seedling; for cut flowers, garden decoration and pot forcing.

Class: Hybrid polyantha.

Breeding: Seedling.

*Seed parent.*—"Rosemary."

*Pollen parent.*—An unnamed seedling of "Sweetheart" × an unnamed polyantha seedling.

Propagation: Holds its distinguishing characteristics through succeeding propagations by budding.

*Flower*

Locality where grown and observed: West Grove, Pennsylvania, U. S. A.

Flowers borne: Several to stem; in irregular flat clusters; on stems of medium length and normal strength.

Quantity of bloom: Free, in greenhouse.

Continuity: Continuous.

Fragrance: Slight.

Bud:

*Peduncle.*—Medium length; medium caliper; stiff; rough; with medium number of red hairs. Color—Oxblood Red, Plate 00823.

*Before calyx breaks.*—Size—from small to medium. Form—medium length; ovoid; with a conspicuous neck; with foliaceous appendages on the surface of the bud; with slender, entire, foliaceous parts extending beyond the tip of the bud equal to ½ or more of its length.

*As calyx breaks.*—Color—Ruby Red, Plate 827, margined with Erythrite Red, Plate 0027.

*As first petal opens.*—Size—medium. Form—medium length; ovoid. Color: outside—Rose Red, Plate 724/3, irregularly overlaid with Rose Red, Plate 724; inside—Rose Red, Plate 724, grading to Rose Red, Plate 724/3 at base of petal.

*Opening.*—Opens up well.

Bloom:

*Size (when fully open).*—Medium; from 2¼ inches to 2½ inches.

*Petalage.*—Very double; from 45 to 55 petals; arranged irregularly.

*Form.*—Very full at first, but becoming flat; petals being at first very loosely rolled outward, but becoming loosely rolled outward at maturity.

Petals:

*Texture.*—Leathery; with inside velvety and outside velvety and very slightly hirsute.

*Shape.*—Outer—round, with one shallow notch. Intermediate—obovate. Inner—obovate.

This description of a newly opened flower was made from a rose grown outdoors in the month of September at West Grove, Pennsylvania, U. S. A.:

*Color.*—Outer petal: outside surface—Spirea Red, Plate 025/1, irregularly overlaid with Tyrian Purple, Plate 727, and with point of attachment Pod Green, Plate 061/3; inside surface—Tyrian Purple, Plate 727, grading to Tyrian Purple, Plate 727/3 at base, with point of attachment Uranium Green, Plate 63/3. Intermediate petal: outside surface—Spirea Red, Plate 025/1, with point of attachment Pod Green, Plate 061/3; inside surface—Spirea Red, Plate 025, grading to Spirea Red, Plate 025/1 towards base, with point of attachment Uranium Green, Plate 63/3. Inner petal: outside surface—Spirea Red, Plate 025/1, with point of attachment Pod Green, Plate 061/3; inside surface—Spirea Red, Plate 025/1, with point of attachment Uranium Green, Plate 63/3.

This description was made from a rose that was open for three days outdoors in the month of September at West Grove, Pennsylvania, U. S. A.:

*Color.*—Outer petal: outside surface—Intermediate Tyrian Rose, Plate 24/1 and Tyrian Rose, Plate 24/2, with occasional blotches of Rose Bengal, Plate 25, and with point of attachment Uranium Green, Plate 63/3; inside surface—Magenta Rose, Plate 027/2, blotched and veined with Tyrian Purple, Plate 727/1, and with point of attachment Pod Green, Plate 061/3. Inner petal: outside surface—Spirea Red, Plate 025/1, with point of attachment Uranium Green, Plate 63/3; inside surface—Spirea Red, Plate 025/1, with point of attachment Pod Green, Plate 061/3.

*General color effect.*—Newly opened flower—Spirea Red, Plate 025/1. 3 days open—Spirea Red, Plate 025/1 at center of bloom, with perimeter Magenta Rose, Plate 027/2.

*Behavior.*—Drop off cleanly; persist at times.

*Flower longevity.*—On bush in garden—8 days in September. Cut roses grown outdoors and kept at living-room temperatures—6 days in September.

*Reproductive organs*

Stamens: Very few; arranged irregularly about pistils; mixed with petaloids.

Filaments: Few; most with anthers; medium length, Color—Sap Green, Plate 62/2.

Anthers: All open at once; medium size; seldom an anther fused with a petaloid. Color—Rhodonite Red, Plate 0022.

Pollen: Moderate.

Pistils: Few.

Styles: Uneven; medium length; medium caliper; loosely bunched.

Stigma: Color—white.

Ovaries: All enclosed in receptacle.

Hips: None.

Sepals: Permanent; moderately long; spear-shaped.

Seeds: None.

*Plant*

Foliage:

*Leaves.*—Compound of 5 and sometimes 7 leaflets; normal abundance; medium size; leathery.

*Leaflets.*—Shape—round, with apex acuminate. Base—round. Margin—simply serrate.

*Color.*—Mature: upper surface—Parsley Green, Plate 00962; under surface—Lavender Green, Plate 000761. Young: upper surface—Parsley Green, Plate 00962, overlaid at edge of base with Maroon, Plate 1030; under surface—Sage Green, Plate 000861/1, very lightly overlaid in places with Garnet Brown, Plate 00918/3.

*Rachis (the supporting stem of the compound leaf).*—Medium caliper. Upper side—grooved; hairy. Under side—sparsely prickly.

*Stipules.*—Medium length; narrow; with points of medium length turning out at an angle of more than 45°.

*Disease resistance.*—Comparable to that of the average variety grown under the same cultural conditions at West Grove, Pennsylvania, U. S. A.

Growth:

*Habit.*—Bushy; upright; much-branched.

*Growth.*—Free.

*Canes.*—Medium caliper.

*Main stems.*—Bright. Color—Spinach Green, Plate 0960/1. Prickles—several; color—Garnet Brown, Plate 00918/3. Hairs—none.

*Branches.*—Bright. Color Spinach Green, Plate 0960/1. Prickles—several; color—Oxblood Red, Plate 00823/3, overlying Fern Green, Plate 0862/2. Hairs—none.

*New shoots.*—Dull. Color—Oxblood Red. Plate 00823. Prickles—several; color—Purple Madder, Plate 1028. Hairs—none.

I claim:

A new and distinct variety of rose plant of the hybrid polyantha class, substantially as herein shown and described, characterized particularly as to novelty by the unique combination of a dense and compact habit of growth, excellent foliage, very free flowering habit, consistent uniform distribution of the blooms on the plant, very double, long-lasting blooms, a distinctive Spirea Red general color tonality of the blooms, and exceptionally good suitability for greenhouse pot forcing.

No references cited.